United States Patent
Osman

(10) Patent No.: US 9,370,379 B2
(45) Date of Patent: Jun. 21, 2016

(54) ENDOSCOPIC SOFT TISSUE WORKING SPACE CREATION

(75) Inventor: Said G. Osman, Frederick, MD (US)

(73) Assignee: Amendia, Inc., Marietta, GA (US)

( * ) Notice: Subject to any disclaimer, the term of this patent is extended or adjusted under 35 U.S.C. 154(b) by 448 days.

(21) Appl. No.: 13/500,330

(22) PCT Filed: Oct. 5, 2010

(86) PCT No.: PCT/US2010/051404
§ 371 (c)(1),
(2), (4) Date: Apr. 5, 2012

(87) PCT Pub. No.: WO2011/044084
PCT Pub. Date: Apr. 14, 2011

(65) Prior Publication Data
US 2012/0203071 A1    Aug. 9, 2012

Related U.S. Application Data

(60) Provisional application No. 61/248,664, filed on Oct. 5, 2009.

(51) Int. Cl.
| | | |
|---|---|---|
| A61B 1/32 | (2006.01) | |
| A61B 17/34 | (2006.01) | |
| A61B 17/02 | (2006.01) | |
| A61B 17/00 | (2006.01) | |

(52) U.S. Cl.
CPC ......... *A61B 17/3421* (2013.01); *A61B 17/0218* (2013.01); *A61B 2017/00557* (2013.01); *A61B 2017/3484* (2013.01)

(58) Field of Classification Search
CPC ........... A61B 17/0218; A61B 17/3421; A61B 2017/00557; A61B 2017/3484
USPC ................................. 606/200, 198, 104–109
See application file for complete search history.

(56) References Cited

U.S. PATENT DOCUMENTS

| | | | |
|---|---|---|---|
| 5,345,927 A * | 9/1994 | Bonutti | 600/207 |
| 7,179,225 B2 | 2/2007 | Shluzas et al. | |
| 7,311,719 B2 | 12/2007 | Bonutti | |
| 2006/0036264 A1 | 2/2006 | Selover et al. | |

\* cited by examiner

*Primary Examiner* — Anu Ramana
*Assistant Examiner* — Jessica Weiss
(74) *Attorney, Agent, or Firm* — David L. King

(57) ABSTRACT

A device for creating endoscopic operating space includes an external cannula, an internal cannula disposed in the external cannula, and an expandable retractor disposed at a distal end of the device and cooperable with the external cannula and the internal cannula. The expandable retractor is displaceable between an unexpanded position and an expanded position. An actuator is cooperable with the expandable retractor to displace the expandable retractor between the unexpanded position and the expanded position.

4 Claims, 5 Drawing Sheets

ENDOSCOPIC SOFT TISSUE WORKING SPACE CREATION

CROSS-REFERENCES TO RELATED APPLICATIONS

This application is the U.S. national phase of International Application No. PCT/US2010/051404 filed 5 Oct. 2010 which designated the U.S. and claims priority to U.S. Provisional Patent Application Serial No. 61/248,664 filed 5 Oct. 2009, the entire contents of each of which are hereby incorporated by reference.

BACKGROUND OF THE INVENTION

Most endoscopic procedures involve operation in natural cavities. Examples include laparoscopy, thoracoscopy, cystoscopy, arthroscopy, bronchoscopy, esophago-gastroduodenoscopy, colonoscopy, colopscopy and hysteroscopy. Most other procedures, until recently have been performed through formal open procedures. Arthroscopy of the intervertebral disc has been practiced for nearly three decades now, but the disc space is a syndesmosis and lacks joint cavity. Attempts have been made to create an operating space in the retroperitoneal area to perform minimally invasive fusion of the lumbar spine. Arthroscopic Subacromial decompression is not an intra-cavitary procedure although one may start in the subacromial bursa.

With the successes of endoscopic procedures in most specialties of surgery, there is an increasing demand by patients for less invasive procedures, and efforts are being made by specialists in all surgical fields to find ways to satisfy this demand. When successful, the benefits are tremendous: the surgical time may be drastically reduced; surgical trauma is invariably less with endoscopic approaches; intra-operative and post-operative blood loss is usually minimal; hospital stay is short; rehabilitation is short and more complete than in cases of conventional procedures; the need for pain medication is less both in terms of the strength and duration of the medication; and return to productive activities is much earlier in most cases. In areas where there is no natural cavity, mini-open procedures are often performed to minimize surgical trauma and blood loss, but the trade-off may be a technically difficult procedure with less than satisfactory median or long term clinical outcome. While not always feasible, a new approach whereby an artificial working space is created to mimic a natural cavity, where one does not exist, is possible in many areas especially in the field of orthopedic and spine surgery, to facilitate endoscopic procedures such as anterior and posterior cervical spine procedures; posterolateral fusion of the lumbar spine, bone grafting of non-unions, repair of ruptured tendons and similar procedures.

SUMMARY OF THE INVENTION

The device according to described embodiments provides for minimally invasive operating space. In one arrangement, the device may include a cannula with an expandable retractor at one end. The external end is equipped with gadgets currently used for endoscopic procedures. A similar device may be inserted from the opposite side such that the two cannulas are in contact or nearly in contact at the site of the desired working space. Once inside the body—in the required location—the retractors are expanded, and traction is applied to each cannula in the opposite direction to create a cylindrical space between them. The traction on each cannula is maintained using a variety of techniques. The tubular space in the cannulas is then used as the access portal for the endoscope and instruments to perform the intended procedure.

In an exemplary embodiment, a device for creating endoscopic operating space includes an external cannula, an internal cannula disposed in the external cannula, and an expandable retractor disposed at a distal end of the device and cooperable with the external cannula and the internal cannula. The expandable retractor is displaceable between an unexpanded position and an expanded position. An actuator is cooperable with the expandable retractor to displace the expandable retractor between the unexpanded position and the expanded position.

In one arrangement, the internal cannula is displaceable longitudinally relative to the external cannula, and the actuator displaces the internal cannula relative to the external cannula to thereby displace the expandable retractor between the unexpanded position and the expanded position. In this context, the expandable retractor may include a first part-cone member secured to a distal end of the external cannula and a second part-cone member secured to a distal end of the internal cannula, where the first and second cone members are secured to each other at distal ends thereof. Still further, the actuator may include threads at a proximal end of the internal cannula and a mechanical expander engaging the threads, where rotation of the mechanical expander effects longitudinal displacement of the internal cannula relative to the external cannula. At the second cone member may include reinforcing ribs. Preferably, the retractor is formed of a synthetic fabric or a metal alloy or another biologically compatible material.

In another arrangement, the expandable retractor includes a plurality of extensions secured to a distal end of the internal cannula, a cap secured over a distal end of the external cannula and having through holes through which the plurality of extensions are movable, and a membrane positioned over the cap. In the unexpanded position, distal ends of the extensions are positioned flush with or adjacent the cap and the membrane is collapsed. In the expanded position, the internal cannula is longitudinally displaced relative to the external cannula, the extensions are positioned through the through holes, and the membrane is expanded and covering the extensions.

The expandable retractor may alternatively include an extension of the external cannula, where a proximal end of the extension includes an inside diameter that is narrower than an outside diameter of the internal cannula. When the internal cannula is longitudinally displaced relative to the external cannula, the internal cannula engages the proximal end of the extension to displace the expandable retractor to the expanded position The external cannula and the internal cannula may be formed in one piece with a channel therebetween, where the expandable retractor includes a balloon attached to a distal end of the external and internal cannula. In this context, the actuator may include a source of fluid in fluid communication with the balloon via the channel. Moreover, a wall of the balloon may have a varied thickness such that when the balloon is inflated to the expanded position, a distal surface of the balloon expands less than a proximal wall of the balloon.

Preferably, the external cannula and the internal cannula are formed of a metal alloy or a biocompatible plastic material.

In another exemplary embodiment, a method of creating endoscopic operating space using the device of the described embodiments includes the steps of, with the expandable retractor in the unexpanded position, positioning the device within a tissue space in which the endoscopic operating space is to be created; displacing with the actuator the expandable retractor to the expanded position; and applying traction to the device with the expandable retractor in the expanded position. The method may further include positioning a second one of the device on an opposite side in the tissue space, where the step of applying traction includes applying traction to both devices in opposite directions.

BRIEF DESCRIPTION OF THE DRAWINGS

These and other aspects and advantages will be described in detail with reference to the accompanying drawings, in which:

FIGS. 1A1 and 1B1 show respective end views of figures 1A and 1B;

FIGS. 4A1 and 4B1 show respective end views of FIGS. 4A and 4B.

DETAILED DESCRIPTION OF THE INVENTION

Figure 1A:
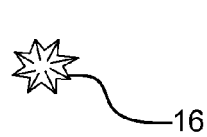
FIGS. 1A and 1B show a first exemplary embodiment of the device for creating endoscopic operating space.
Figure 1A:
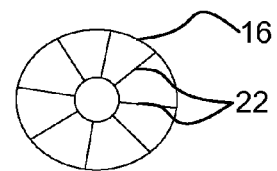
Figure 1A:
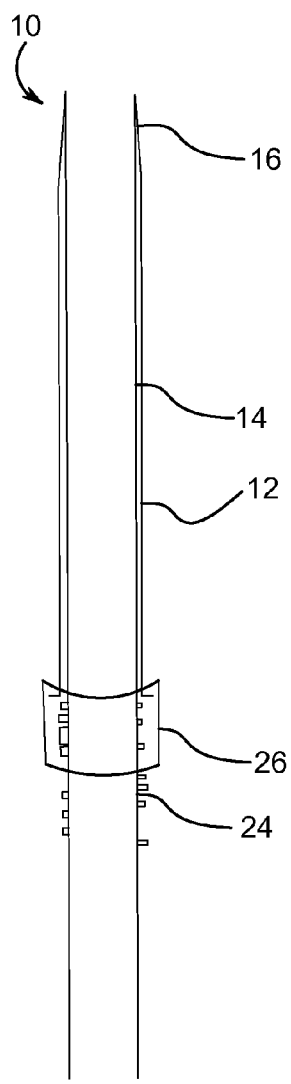
Figure 1B:
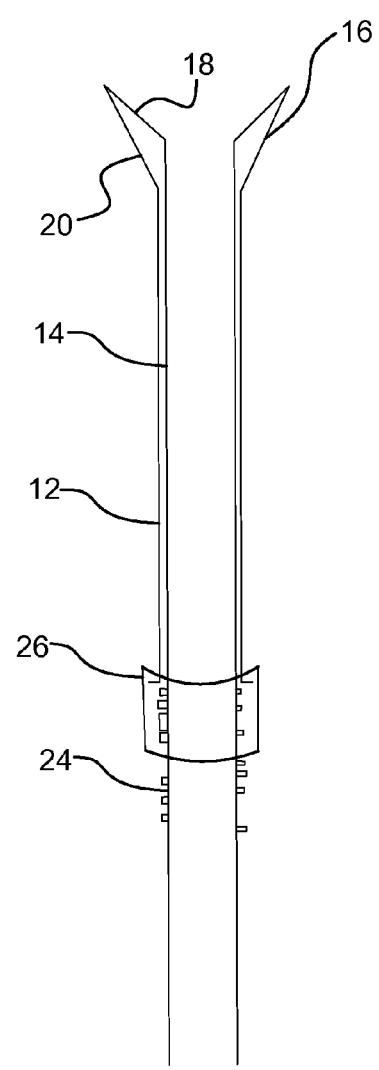

The device of the described embodiments includes a cannula with a distal end (the end inside the body) which is armed with an expandable retractor, and the proximal end (the end outside the body) which is armed with gadgets such as irrigation/suction portal, and water-seal to prevent back-leakage of the irrigation fluid. In a preferred embodiment, referring to FIGS. 1A, 1A1 and 1B, 1B1 the cannula system 10 is made of an external cannula 12 and an internal cannula 14 which may be made out of a metal alloy or a biocompatible plastic material. The two cannulas 12, 14 fit into each other. At the distal ends, the cannulas are attached to the retractor 16 which, in an unexpanded state is folded in a manner similar to a non-deployed umbrella. The retractor 16 is made of two cones, one 18 fitting inside the other 20, and with the tips or summits cut off (i.e., part-cones) to permit attachments to the distal ends of the two cannulas 12, 14, which are fitted into each other. The distal ends of the cones 18, 20, i.e., the bases, are attached to each other by any technique currently in general practice, such that the junction will act as a hinge around which the expansion and closure of the retractor 16 can take place. Further, the walls of the retractor 16 may be reinforced radially with ribs 22 made of the same or different material as the retractor. The wall of the retractor 16 may be made of a synthetic fabric or metal alloy or any other material that is biologically compatible.

Near the proximal end of the inner cannula 14, at its point of exit from the outer cannula 12, the inner cannula 14 is threaded. The threads 24 fit into the threads of a mechanical expander 26, which is attached to the outer cannula 12, but allowed to freely rotate on it without being decoupled from it. Hence, by spinning the mechanical expander 26 in one direction, the inner cannula 14 extends beyond the distal end of the outer cannula 12 forcing the retractor 16 to expand. Conversely, by spinning the expander 26 in the opposite direction, the retractor 16 folds like a non-deployed umbrella. Any other mechanism of expansion/closure may be used to achieve the desired goal of expansion and folding of the retractor 16. Moreover, threads acting as guy-ropes running inside tubular channels in the wall of a single cannula can achieve the same goal.

Figure 2A:
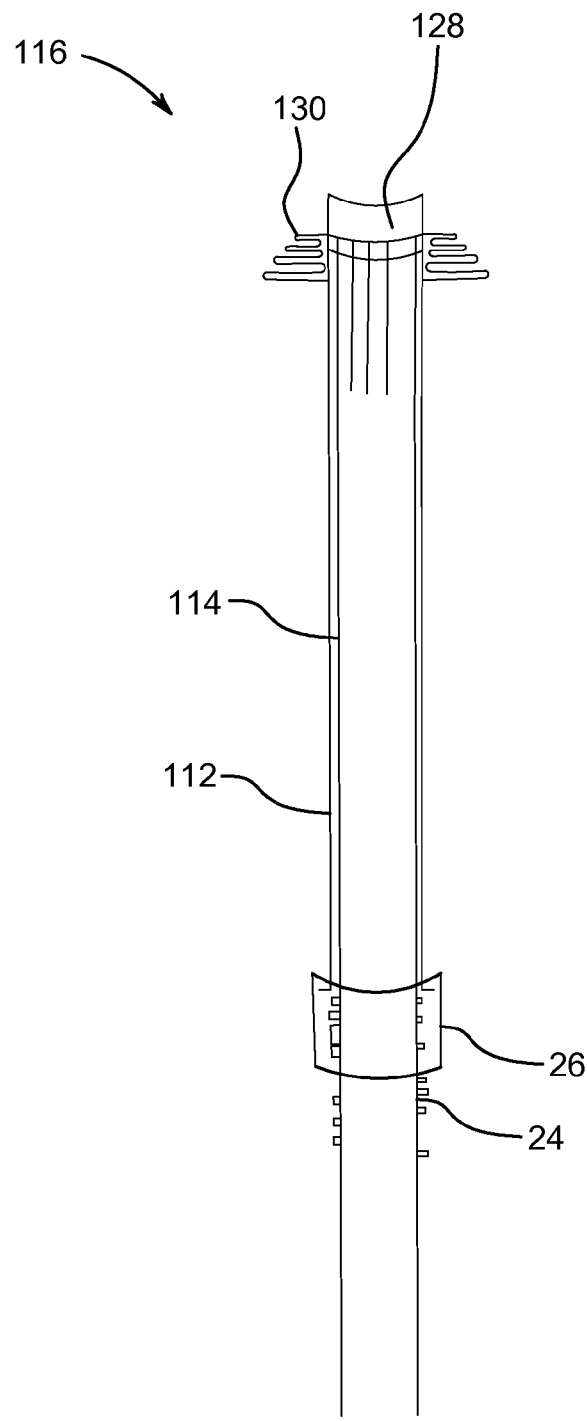
FIGS. 2A and 2B show an embodiment with a membrane over the extension members.
Figure 2B:
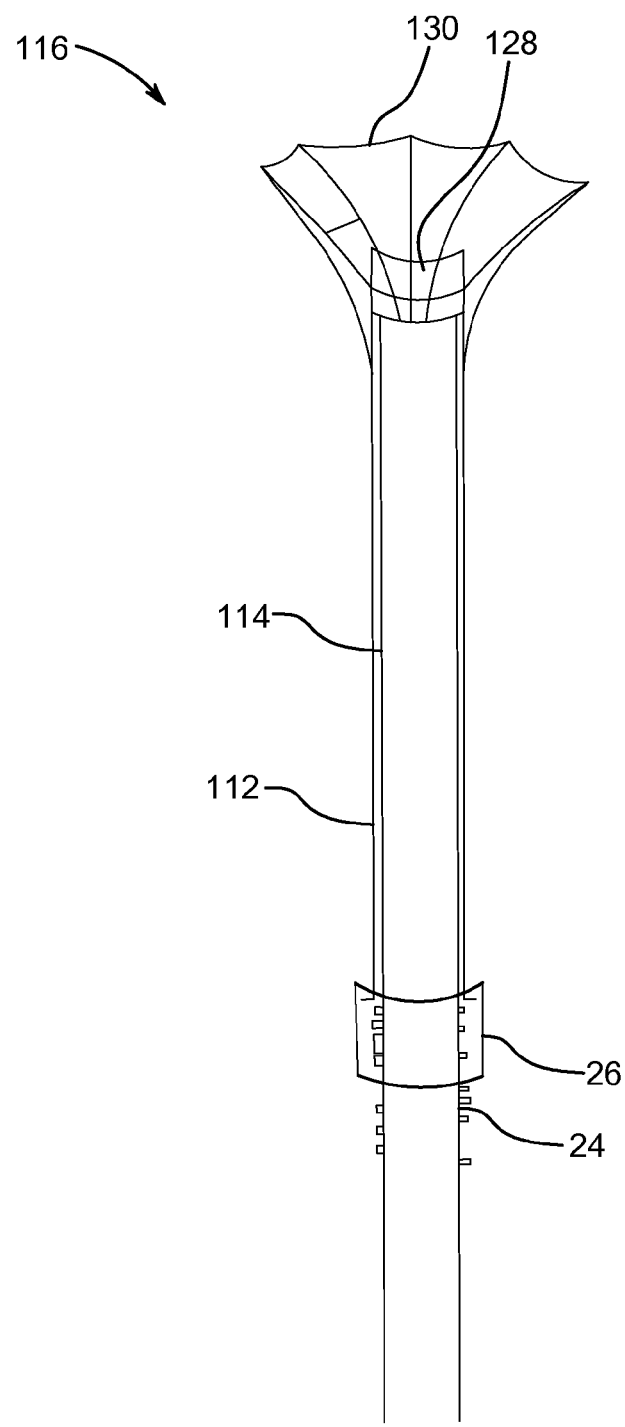

In another embodiment, with reference to FIGS. 2A and 2B, the retractor 116 comprises a plurality of extensions attached to the distal end of the inner cannula 114. The tips of the extensions exit through holes in a cap 128 secured to the distal end of the outer cannula 112. In the non-deployed state, the tips of the extensions are not protruding out of the outer cannula cap 128 but are flush with or adjacent its wall. Tips of the retractor 116 are attached to a membrane 130 of fine synthetic fabric, which may be made in the shape of a cone with the base attached to the retractor tips and the narrower end attached to the outer wall of the outer cannula 112. The retractor 116 may be deployed into expansion by using the same or similar mechanism 24, 26 as described in the first embodiment. As the device is protracted, the membrane 130 is pulled up from a collapsed position and draped over the extending retractor 116 into an extended position. The synthetic membrane 130 is designed to prevent intrusion of the soft tissue between the radially arranged ribs of the retractor. The cap 128 on the end of the outer cannula 112 is open-ended such than the cannulated device can be used as an operating channel.

Figure 3A:
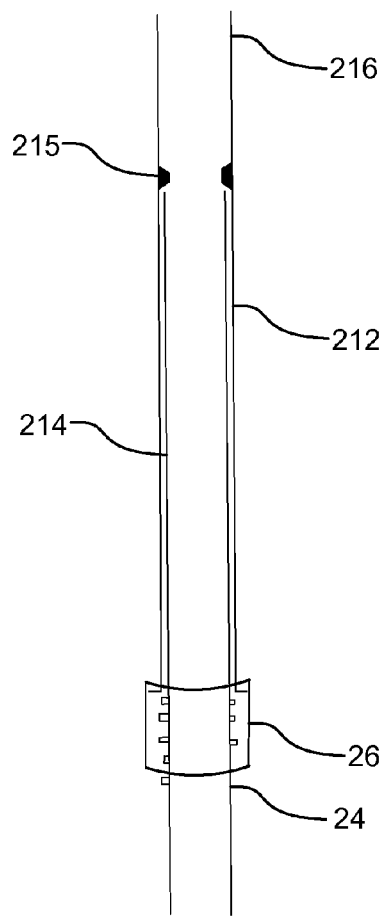
FIGS. 3A and 3B show an embodiment where the retractor is an extension of the external cannula.
Figure 3B:
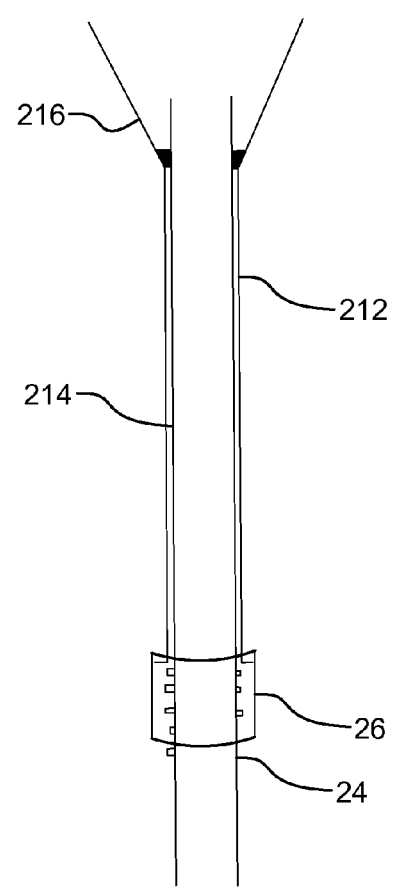

In another embodiment, with reference to FIGS. 3A and 3B, the retractor 216 may be the extension of the outer cannula 212. The cylindrical extension may be split vertically into a plurality of extension pieces and joined to the end of the cannula by a variety of methods which permit rotation of the pieces in a manner that widens or narrows the diameter of the retractor. Proximal ends 215 of the extensions are arranged such that the diameter is smaller than the inner cannula diameter, and cover the distal end of the inner cannula 214, such that when the inner cannula 214 is advanced distally by the mechanism previously described, the individual extensions will rotate outward retracting the surrounding tissues. The individual extension may be joined to its neighbors with membranes made out of fine but strong synthetic fabrics.

Figure 4A:
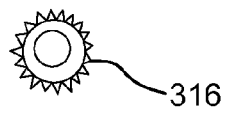
FIGS. 4A and 4B show an embodiment using a balloon retractor.
Figure 4A:
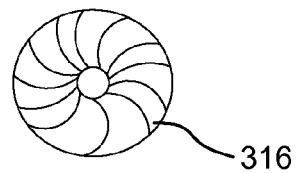
Figure 4A:
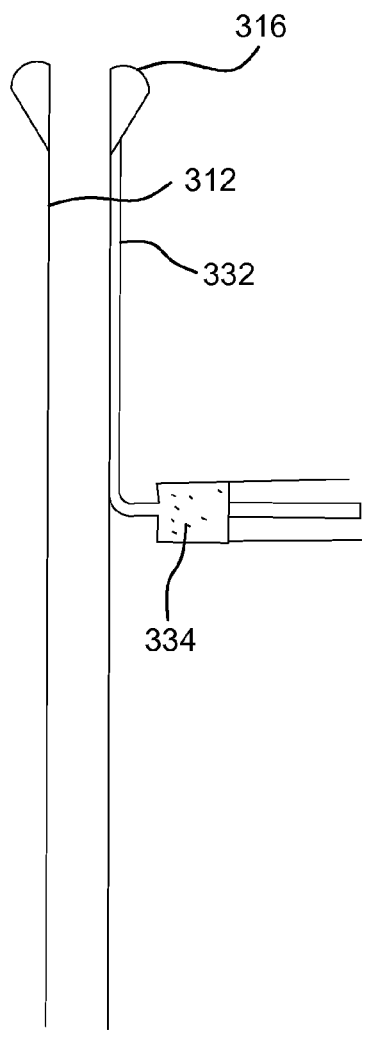
Figure 4B:
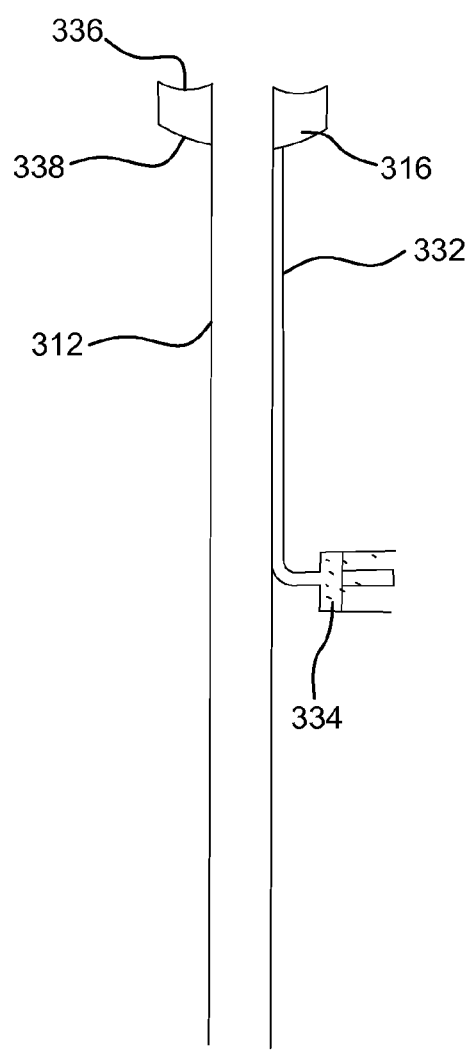

In yet another configuration, with reference to FIGS. 4A, 4A1 and 4B, 4B1 the cannulas are combined to act as a single cannula 312 with a balloon 316 attached at its distal end, which may be used to create soft tissue distraction. The balloon 316 is in fluid communication with an inflation/deflation channel 332 which runs in the wall of the cannula 312 and exits at some distance from the proximal tip of the cannula. The channel 332 ends in a nozzle with a Leur lock and is attached to a fluid source 334 such as syringe. Fluid or air may be used to inflate the retractor 316. The balloon, which is preferably made out of a biocompatible synthetic material, has a wall which is differentially thickened such that when it is inflated, its distal wall 336 stretches less than the proximal wall 338, such that when inflated its distal surface remains relatively flat. Two cannulas may be deployed into the desired area, and after inflation, a three-way valve is deployed to maintain the inflation. Traction is applied in opposite directions to create a cylindrical working space between them.

A variation of the above concept involves embedding the balloon in the wall of the cannula near its distal end. The inflation channel runs from the interior of the balloon, inside the cannula wall and exits the wall near the proximal end of the cannula where it ends in a nozzle. When inflated, the balloon forms a ring near the distal end of the cannula, performing the task of retraction. A further variation of this embodiment is where the balloon, in a cylindrical configuration, overlies the distal end of the cannula. It is covered by strips of material of which the wall is made. The strips proximally form junctions with the cannula wall, and are freeended distally. When the balloon is inflated, the extension strips open up, retracting the soft tissue.

APPLICATION OF THE INVENTION

Generically, the device may be applied in any tissue space as long as the anatomy permits, but two applications in the spine are described here.

A. Postero-lateral endoscopic fusion of the lumbar spine. The patient is prepared for surgery in the routine fashion and after induction of endotracheal anesthesia, is placed in prone position on the operating table.
  a. Fluoroscopic imaging is used to locate the level of the target transverse processes. The levels are marked on both sides of the spine.
  b. Portal sites are chosen on each side of the mid-line such that instrumentation through the sites will permit triangulation at the mid-point between the transverse processes.
  c. Tissue dilators are inserted through the portals, aiming the tips of the dilators to the mid-point of the inter-transverse line.
  d. Two cannulas bearing the retractors in a non-expanded state are introduced over the dilators into the inter-transverse position.
  e. The retractors are deployed in the manner described above, depending on the design.
  f. Manual traction of the cannulas is performed in opposite directions to create a cylindrical space between the ends of the cannulas. Traction of each cannula is maintained by application of a stopper on the cannula at the level of the skin or by attaching the cannula to a holding frame, which in turn may be attached to the operating table or through an adhesive or other means to the patient's torso.
  g. The dilators are removed, and the irrigation and suction systems are attached to the cannulas as is currently practiced in arthroscopy.
  h. The arthroscope is inserted through one portal, and the instruments through the other.
  i. The soft tissue may be debrided from the intertransverse space, the transverse processes and the lateral walls of the superior articular processes with graspers, shavers, and diathermy. Subperiosteal dissection of the transverse processes and the neighboring bony structures is performed with curettes and other appropriate instruments
  j. Automated tools such as diamond burrs and manual instruments such as fine gauges may be used to decorticate the graft bed.
  k. The arthroscope and the instruments may be transposed to accomplish this task.
  l. The graft material (autogenous bone, allografts and bone substitutes) may then be laid on the prepared graft bed. Similar procedures may be repeated for the contralateral side.

It is to be noted that the same portals may be used for minimally decompressing the for animal and the spinal canals. By the same token, the same portals may be used to implant the pedicle screws using minimally invasive approach. Thus, through two or three small incisions—each one centimeter or less—decompression of the spine; postero-lateral fusion; and pedicle screw implantation may be accomplished.

B. Retro-pharyngeal/esophageal Endoscopic Cervical Spine Procedures.

Because of the overhang by the lateral masses, the vertebral artery which runs through the foramen transversoria, the dis- proportionately large cervical nerve roots as compared to the sizes of the cervical discs, and the uncinate process which obstruct access to the posterolateral corner of the cervical intervertebral discs, the posterolateral arthroscopic approach to the cervical spine is simply impractical and dangerous. The anterolateral approach, on the other hand, is practical and is currently used for simple discectomies and annuloplasties. In the current invention, the following is an exemplary method of practice for both intra-discal and prevertebral procedures:
  a. The patient is placed in supine position with a bolster between the shoulder blades to place the neck in extension.
  b. The fluoroscope is angulated in the cephalo-caudal direction to visualize the target disc space in the plane parallel to its inclination.
  c. Portal sites are marked under fluoroscopic control on either side of the midline, as currently practiced.
  d. A stab incision is made at the selected portal site, and a spinal needle is introduced as currently practiced.
  e. The stylet is removed, and the guide wire is introduced into the disc through the spinal needle.
  f. The dilator and the cannula are inserted over the guide wire until the disc is contacted.
  g. For intra-discal procedures, the guide-wire and the dilator are removed while holding the cannula in place against the annulus, and trephine is used to perform annulotomy.
  h. The cannula is docked into the disc under fluoroscopic control, and the necessary intra-discal procedure is performed.
  i. For the retro-esophagial/prevertebral procedures, the cannula is pulled out of the disc and the retractor is deployed as described above, or if the cannula is not armed with the retractor, an exchange of the cannulas is performed over the re-introduced dilator—replacing a plain cannula with one armed with a retractor.
  j. Having deployed the cannula-retractor system bilaterally, traction is applied as previously described to create a cylindrical space between the two retractors.
  k. The athroscope is introduced through one portal and the instruments through the other after establishing the irrigation/suction system.
  l. Pre-vertebral steps in the procedure may now be undertaken—e.g. anchoring of an intra-discal device, removal of osteophytes or other structures.

This approach may be used to perform thyroidectomies and similar procedures in the neck.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A device for creating endoscopic operating space, the device comprising: an external cannula; an internal cannula disposed in the external cannula; an expandable retractor disposed at a distal end of the device and cooperable with the external cannula and the internal cannula, the expandable retractor being displaceable between an unexpanded position and an expanded position; an actuator cooperable with the expandable retractor, the actuator displacing the expandable retractor between the unexpanded position and the expanded position; wherein the internal cannula is displaceable longitudinally relative to the external cannula, and wherein the actuator displaces a distal end of the internal cannula outward past a distal end of the external cannula to thereby displace the expandable retractor from the unexpanded position to the expanded position; wherein the expandable retractor comprises a plurality of reinforcing ribs and walls connected continuously between the ribs, wherein the walls of the expandable retractor are a membrane formed of a synthetic fabric, and when in the unexpanded position, the membrane has folds positioned below the ribs, expansion of the folds of the membrane outwardly with respect to a longitudinal axis of the internal or external cannula causing the plurality of ribs of the expandable retractor to move to the expanded position to form an operating space; and wherein the expandable retractor comprises a first part-cone member secured directly to the distal end of the external cannula and a second part-cone member secured directly to the distal end of the internal cannula, the first and second part-cone members being secured to each other at distal ends thereof, wherein at least the second part-cone member comprises the reinforcing ribs; and wherein the actuator comprises threads at a proximal end of the internal cannula and a mechanical expander engaging the threads, wherein rotation of the mechanical expander effects longitudinal displacement of the internal cannula relative to the external cannula.

2. A device according to claim 1, wherein the external cannula and the internal cannula are formed of a metal alloy or a biocompatible plastic material.

3. A method of creating an endoscopic operating space using a device including an external cannula, an internal cannula disposed in the external cannula, an expandable retractor disposed at a distal end of the device and displaceable between an unexpanded position and an expanded position, and an actuator cooperable with the expandable retractor, the method comprising: with the expandable retractor in the unexpanded position, positioning the device within a tissue space in which the endoscopic operating space is to be created; displacing with the actuator the expandable retractor to the expanded position; applying traction to the device with the expandable retractor in the expanded position, wherein the internal cannula is displaceable longitudinally relative to the external cannula, and wherein the step of displacing the expandable retractor comprises displacing with the actuator the internal cannula relative to the external cannula such that a distal end of the internal cannula is displaced outward past a distal end of the external cannula to thereby displace the expandable retractor from the unexpanded position to the expanded position; wherein the expandable retractor comprises a plurality of reinforcing ribs and walls connected continuously between the ribs, wherein the walls of the expandable retractor are a membrane formed of a synthetic fabric, and when in the unexpanded position, the membrane has folds positioned below the ribs, expansion of the folds of the membrane outwardly with respect to a longitudinal axis of the internal or external cannula causing the plurality of ribs of the expandable retractor to move to the expanded position to form an operating space; and wherein the expandable retractor comprises a first part-cone member secured directly to the distal end of the external cannula and a second part-cone member secured directly to the distal end of the internal cannula, the first and second part-cone members being secured to each other at distal ends thereof, wherein at least the second part-cone member comprises the reinforcing ribs; and wherein the actuator comprises threads at a proximal end of the internal cannula and a mechanical expander engaging the threads, wherein rotation of the mechanical expander effects longitudinal displacement of the internal cannula relative to the external cannula.

4. A method according to claim 3, further comprising positioning a second one of the device on an opposite side in the tissue space, and wherein the step of applying traction comprises applying traction to both devices in opposite directions.

* * * * *